US007858765B2

(12) United States Patent
Soto-Jara et al.

(10) Patent No.: US 7,858,765 B2
(45) Date of Patent: Dec. 28, 2010

(54) OX40R BINDING AGENTS

(75) Inventors: Claudio Soto-Jara, Friendswood, TX (US); Claudia Pena-Rossi, Geneva (CH)

(73) Assignee: Merck Serono SA, Coinsins, Vaud (CH)

( * ) Notice: Subject to any disclaimer, the term of this patent is extended or adjusted under 35 U.S.C. 154(b) by 0 days.

(21) Appl. No.: 12/624,534

(22) Filed: Nov. 24, 2009

(65) Prior Publication Data

US 2010/0136628 A1 Jun. 3, 2010

Related U.S. Application Data

(62) Division of application No. 10/510,015, filed as application No. PCT/EP03/50089 on Apr. 2, 2003, now Pat. No. 7,758,852.

(30) Foreign Application Priority Data

Apr. 3, 2002 (EP) ................................. 02100334

(51) Int. Cl.

| | |
|---|---|
| ***C07H 21/04*** | (2006.01) |
| ***C12N 5/07*** | (2010.01) |
| *C12N 15/00* | (2006.01) |
| *C12P 21/02* | (2006.01) |
| *A61K 39/00* | (2006.01) |
| *A61K 39/385* | (2006.01) |

(52) U.S. Cl. .................. 536/23.1; 536/23.4; 435/252.3; 435/320.1; 435/69.5; 424/192.1; 424/193.1; 424/195.11

(58) Field of Classification Search ....................... None
See application file for complete search history.

(56) References Cited

U.S. PATENT DOCUMENTS

| | | | | |
|---|---|---|---|---|
| 5,866,681 A | 2/1999 | Scarborough | | |
| 6,242,566 B1 * | 6/2001 | Godfrey et al. | ............. | 530/350 |
| 6,602,856 B1 | 8/2003 | Quillan et al. | | |
| 6,872,519 B1 | 3/2005 | Sokoloff et al. | | |

FOREIGN PATENT DOCUMENTS

| | | |
|---|---|---|
| WO | WO 95/21915 | 8/1995 |
| WO | WO 00/58494 | 10/2000 |
| WO | WO 01/57274 | 8/2001 |
| WO | WO 01/72771 | 10/2001 |

OTHER PUBLICATIONS

Chien et al. The two-hybrid system: a method to identify and clone genes for proteins that interact with a protein of interest. Proc. Natl. Acad. Sci. USA, 88, 9578-9582, 1991.*

Allignet, J. et a/. “Sequence of Staphylococcal Plasmid Gene, *vga*, Encoding a Putative ATP-binding Protein Involved in Resistance to Virginiamycin A-like Antibiotics” *Gene*, 1992, pp. 45-51, vol. 117.

Bodmer, J. et al. “The Molecular Architecture of the TNF Superfamily” *Trends in Biochemical Sciences*, Jan. 2002, pp. 19-26, vol. 27, No. 1.

Stüber, E. et al. “The T Cell-B Cell Interaction via OX40-OX4OL Is Necessary for the T Cell-Dependent Humoral Immune Response” *The Journal of Experimental Medicine*, Mar. 1996, pp. 979-989, vol. 183.

Weinberg, A. D. “OX40: Targeted Immunotherapy-Implications for Tempering Autoimmunity and Enhancing Vaccines” *Trends in Immunology*, Feb. 2002, pp. 102-109, vol. 23, No. 2.

Penn, S. G. et al. “Protein #5114 Encoded by Probe for Measuring Heart Cell Gene Expression” Database accession No. ABB23115, XP002211957, Jan. 23, 2002, Database GSP 'Online!

Rosen, C. A. et al. “Human Secreted Protein Sequence Encoded by Gene 39 SEQ ID No. 99” Database accession No. AAB44733, XP002211958, Feb. 12, 2001, Database GSP 'Online!

Beasley, J. et al. “Insulin/Insulin-like Growth Factor Receptor-Binding Peptide #1955” Database accession No. AAU89999, XP002211956, Jun. 18, 2002, Database GSP 'Online!

Isono, T. et al. “Expression of OX40 and OX40 Ligand Genes in Rabbit HTLV-I-Transformed T Cell Lines” Database accession No. 002765, XP002211959, Dec. 15, 1998, Database SWALL 'Online!

* cited by examiner

*Primary Examiner*—Lorraine Spector
*Assistant Examiner*—Elly-Gerald Stoica
(74) *Attorney, Agent, or Firm*—Saliwanchik, Lloyd & Saliwanchik

(57) ABSTRACT

The present invention discloses peptides isolated from the extracellular domain of OX40 Ligand (OX40L) capable of binding OX40 Receptor (OX40R) and inhibiting OX40R-OX40L interaction. Such peptides, fusion proteins comprising them, as well as peptides and other molecules designed on their sequences, can be used as OX40R binding agents competing with natural OX40L for blocking OX40R-mediated cell signaling in the prophylaxis and/or treatment of diseases related to activated T cells.

16 Claims, 7 Drawing Sheets

Figure 2
A)
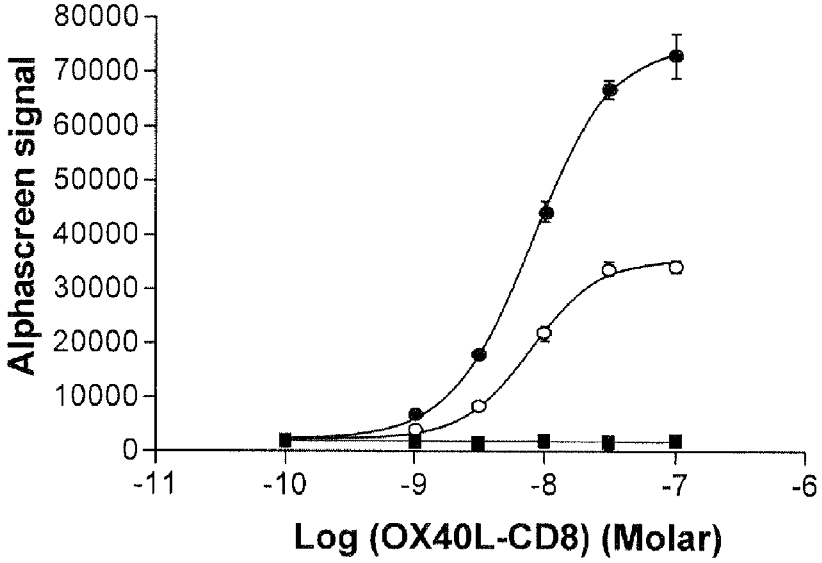
B)
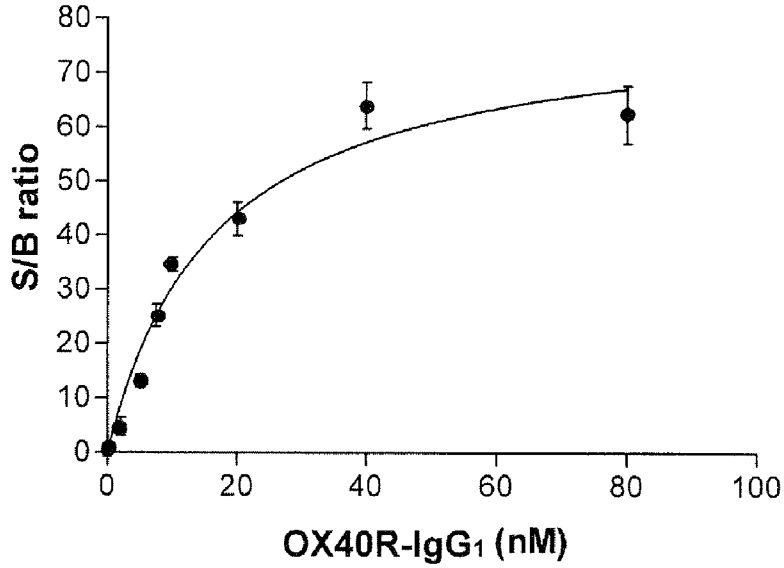

```
◄    Cytoplasmic domain     ►◄     Transmembrane domain     ►
MERVQPLEENVGNAARPRFERNKLLLVASVIQGLGLLLCFTYICLHFSAL       50

◄                  Extracellular domain
QVSHRYPRIQSIKVQFTEYKKEKGFILTSQKEDEIMKVQNNSVIINCDGF      100
 ------------P3---------------
                      ------------P4--------------
                                          --P5---

                   Extracellular domain
YLISLKGYFSQEVNISLHYQKDEEPLFQLKKVRSVNSLMVASLTYKDKVY      150
                                        ----P1-----
P4
--------P5--------------
                 -------------P6----------------
    ---S-F---K-D--FRE-                        AF-----
          P-OX-1                               P-OX-2

         Extracellular domain          ►
LNVTTDNTSLDDFHVNGGELILIHQNPGEFCVL   183
--------P1----------
         ----------P2------------
-T-NAPD-LCE
  P-OX-2
```

B)

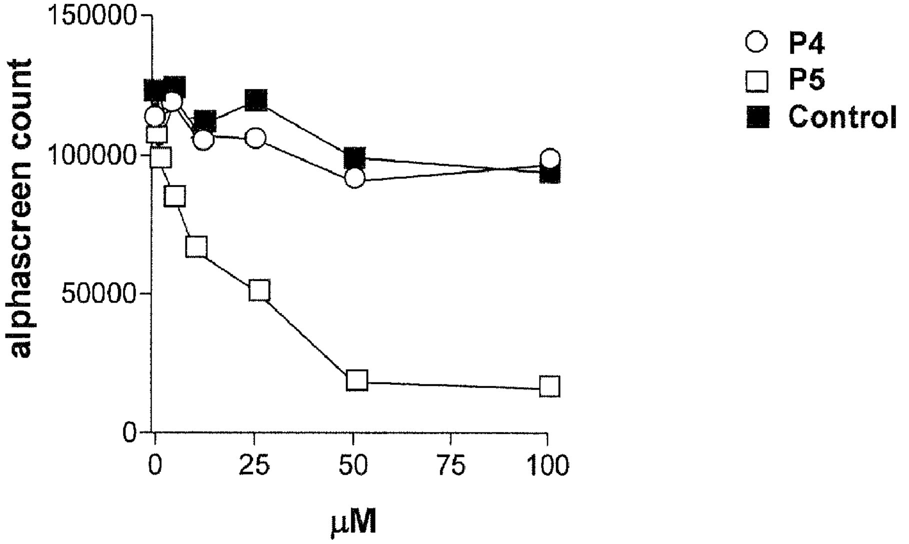

A)

```
P-OX-1            LKGSFFQEVKIDLHFRED     (SEQ ID NO: 14)
                    § §   . §  ..§
P5       IINCDGFYLISLKGYFSQEVNISLHYQKDEE (SEQ ID NO: 6)
P5-1              [GYFSQ]EVNIS            (SEQ ID NO: 8)
P5-2                        ISLHYQKDEE   (SEQ ID NO: 9)
P5-3         GFYLISLKGY                  (SEQ ID NO: 10)
P5-4                     QEVNISLHYQ      (SEQ ID NO: 11)
P5-5     IINCDGFYLI                      (SEQ ID NO: 12)
```

B)

Figure 7
A)
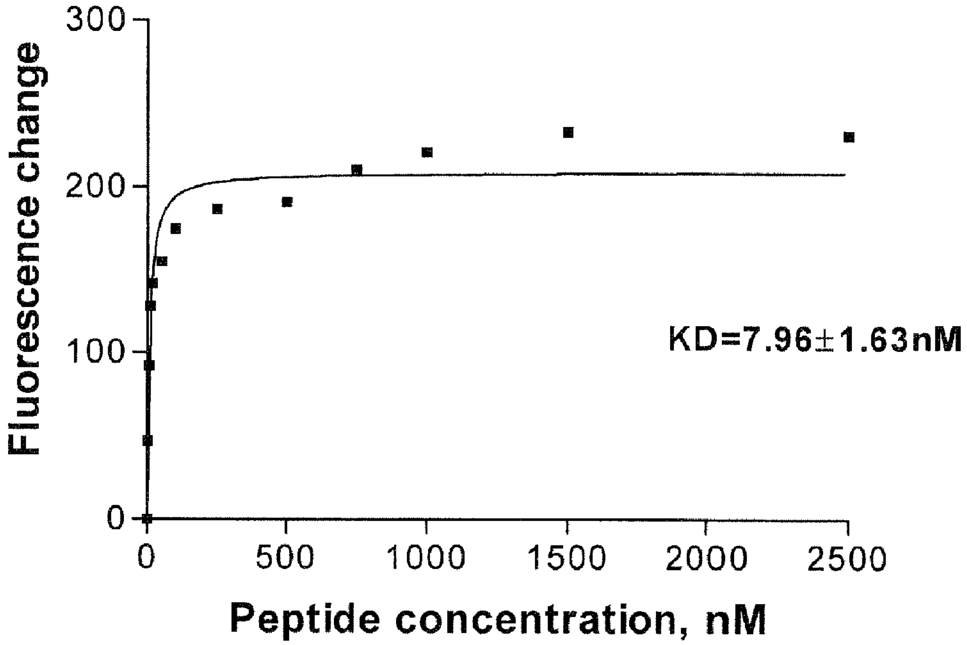
B)
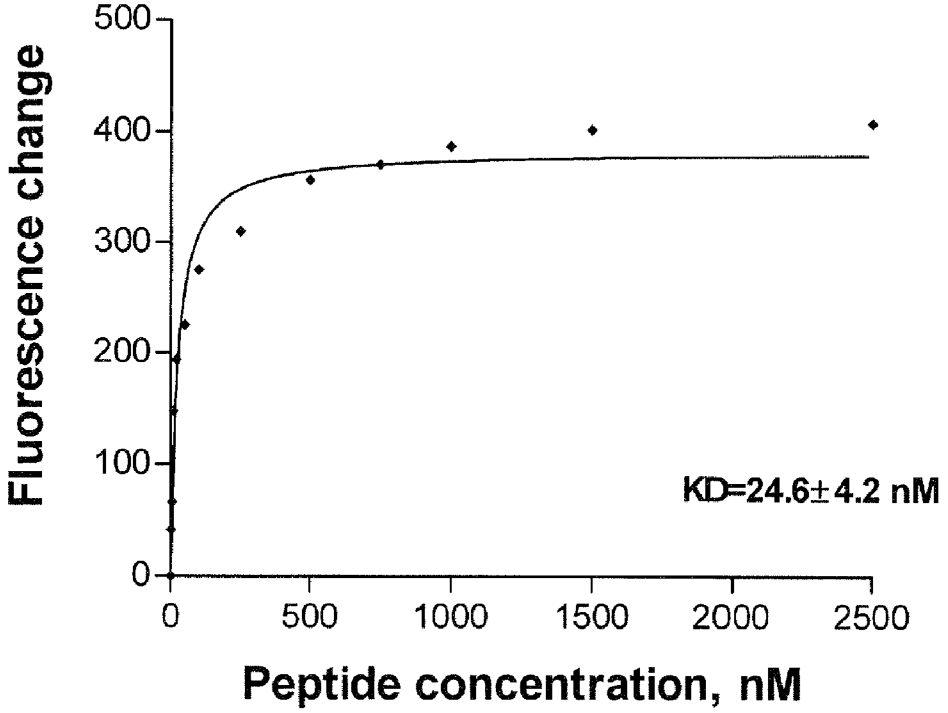

OX40R BINDING AGENTS

CROSS-REFERENCE TO RELATED APPLICATIONS

This application is a divisional of U.S. application Ser. No. 10/510,015, filed Apr. 18, 2006, which is the U.S. national stage application of International Patent Application No. PCT/EP03/50089, filed Apr. 2, 2003.

FIELD OF THE INVENTION

The present invention concerns novel peptides capable of modulating OX40 Receptor-OX40 Ligand interactions.

BACKGROUND OF THE INVENTION

The cell regulatory system constituted by the membrane proteins OX40 Receptor (indicated in the literature also as OX40R, OX-40, OX-40 Antigen, TNFRSF4, or CD134) and OX40 Ligand (indicated in the literature also as OX40L, glycoprotein gp34, ACT-4-L, TNFSF4, CD134 Ligand, or CD134L) has a prominent role in the regulation of immune responses as well as in the formation of secondary lymphoid tissue, similarly to other proteins belonging to the tumor necrosis factor ligand/receptor superfamilies (Gravestein L and Borst J, 1998; Weinberg A, 2002). Many evidences on these activities have been provided by clinical observations and by animal models, for example by gene targeting experiments (Chen A et al., 1999; Kopf M et al., 1999; Murata K et al., 2000).

OX40 Receptor (OX40R, from now on) is a cell surface antigen, member of TNFR family, transiently expressed following T cell receptor (TCR) engagement and acting as a co-stimulatory receptor. It is considered as a highly specific $CD4^+$ or $CD8^+$ activation marker for T cells, being often over-expressed in inflammation sites associated to immunological pathologies, such as in multiple sclerosis or rheumatoid arthritis, as well as in tumor-infiltrating lymphocytes and in the peripheral blood of animal models of graft-versus host disease.

OX40 Ligand (OX40L, from now on) is a transmembrane protein, originally identified as a protein stimulated by human T cell lymphotropic virus 1 infection and CD40 activation (Miura S et al., 1991), having structural similarity to TNF and capable of forming cell-bound or secreted trimers. It is present on activated, antigen-presenting B and T cells, as well as dendritic cells, vascular endothelium cells and other non-hematopoietic tissues (for example heart, skeletal muscle, and pancreas).

OX40L interacts with OX40R as a homotrimer with a high affinity (Kd=0.2-0.4 nM), and various binding assays have been tested on this system (Taylor L et al, 2002; Taylor L and Schwartz H, 2001; Al-Shamkhani A et al., 1997). However, no tridimensional structure has been solved so far, neither detailed structure-activity studies have been performed, in order to provide any further molecular details on the mechanism of OX40L-OX40R interaction.

The interaction between OX40L and OX40R has a co-stimulatory effect to OX40R-expressing effector T cells, leading to a more robust cell responses due to the up-regulation of the cytokine production by T helper cells (Th1 and Th2) and to an increased survival of memory T cells through the inhibition of activation-induced cell death. Confirming evidences were also obtained in the transgenic mice lacking a functional OX40L gene and in autoimmunity animal models, where it was demonstrated that blocking the OX40R-OX40L interaction or depleting OX40R-positive T cells reduces clinical signs of autoimmunity.

Moreover, OX40L induces, upon OX40R binding, the expression of several genes, including the C—C chemokine RANTES, confirming the results obtained in endothelium models where OX40R-OX40L system appears involved in the control of activated T cells extravasation (Kotani A et al., 2002).

Cumulatively, these expression and functional data raise the possibility that the signal transduction pathways regulated by OX40L-OX40R interactions may help to prolong antigen-specific proliferative responses or otherwise influence the persistence, differentiation or reactivation of effector/memory T cell populations.

The interest on OX40R-OX40L system is related to the fact that, even if the intracellular signaling mechanisms have not yet completely understood, the expression profile of OX40R makes this protein a peculiar target for $CD4^+$ T cells mediated diseases in clinical settings, for example in multiple sclerosis, where it is necessary to delete auto-reactive T cells. The hypothesis is that the products modulating OX40R activity may not have the serious side effects of conventional immunosuppressive therapies for autoimmune diseases and transplant rejection, which target all T cells.

The therapeutic potential of modulating the interaction between OX40L and OX40R was recognized by in vivo generated results obtained with OX40L-targeted immunotoxins (Weinberg A et al., 1996), anti-OX40R antibodies (Bansal-Pakala P et al., 2001), anti-OX40L antibodies (Stuber E and Strober W, 1996; Yoshioka Y et al., 2000; Tsukada N et al., 2000), and OX40L-Ig fusion proteins (Higgins L M et al. 1999; Weinberg A et al., 1999). These compounds are intended either to antagonize OX40L-OX40R interaction (for preventing the accumulation of activated $CD4^+$ T cells at inflammatory sites) or to activate OX40R (as in some other pathological conditions, such as cancer).

Various OX40R binding agent, being either agonist or antagonist of OX40R, have been disclosed in the prior art as having positive effects on immunization and cancer treatment (WO 95/21915; WO 95/21251; EP 978287; WO 99/42585; WO 02/66044; U.S. Pat. No. 6,312,700). However, only large molecule such as the OX40L whole extracellular domain or antibodies are actually disclosed as being effective OX40R binding agents. This is also due to the fact that no real structure-activity studies have been performed to characterize this interaction, neither reliable information can be inferred from the analysis of other TNF/TNFR protein structures (Bodmer J L et al., 2002).

Since known OX40R binding agents proved to be useful as therapeutic and diagnostic agents, it would be desirable to identify compounds which, maintaining the binding and OX40L-competing properties of the large molecules above mentioned, are easier to generate and formulate such as peptides or other small molecules.

SUMMARY OF THE INVENTION

It has now been discovered that specific peptides derived from the extracellular domain of OX40L can be used as OX40R binding agents. More specifically, it has been found that a peptide corresponding to amino acids 94-124 of human OX40L, as well as fragments of this peptide comprising amino acids 107-116 of human OX40L, interact with human OX40R with high affinity, as shown by two different reliable screening technologies. Such peptides, heterologous proteins comprising their sequences, as well as peptides and other molecules designed on their sequences, can be used as OX40R binding agents competing with natural OX40L for different therapeutic uses. Other features and advantages of the invention will be apparent from the following detailed description.

DESCRIPTION OF THE FIGURES

FIG. 2: dose-dependent binding of OX40L-CD8 to OX40R-IgG1 as detected using the Alphascreen™ assay. (A) Increasing concentrations of OX40L-CD8 were incubated with OX40R-IgG1 at the concentration of 5 nM (○) or 10 nM (●) for 30 minutes. Biotinylated anti-CD8 antibody (10 nM) was then added and 30 minutes later, streptavidin donor (20 mg/ml) and protein A acceptor (20 mg/ml) beads were added. One hour after these additions, the plate was counted on a Fusion™ reader. Only a very weak signal was detected in the absence of OX40R-IgG1 (■). (B) Effect of increasing OX40R-IgG1 concentration on Signal/Background (S/B) ratio. The S/B ratio was calculated by dividing counts obtained in the presence of OX40L-CD8 (100 nM) by background counts (in the absence of OX40L-CD8). Data are expressed as mean±SEM (Standard Error of the Mean) and all experiments were performed 3 times in triplicate.

FIG. 5: binding of OX40L fragments to OX40R-IgG1. (A) sequence of human OX40L (SWISSPROT Acc. No. P23510; SEQ ID NO: 1), with the indication of the position of main protein domains (on the top of the sequence), together with the sequences corresponding to the peptides tested by the Alphascreen™-based competition assay or the mouse OX40L-derived peptides P-OX-1 (SEQ ID NO: 14) and P-OX-2 (SEQ ID NO: 15) (on the bottom of the sequence; non-identical amino acids are indicated). (B) inhibition of binding of OX40R-IgG1 to OX40L-CD8 by the peptides P4, P5, and a control without any peptide.

FIG. 7: OX40R-IgG1 interaction with peptides P5 (A) and P5-1 (B), as measured by using fluorescence quenching spectroscopy. Non-linear regression analysis of OX40R-IgG1 fluorescence changes reveals a saturable binding with the dissociation constant for the OX40R-IgG1-peptide complex indicated as Kd value for the two peptides.

DETAILED DESCRIPTION OF THE INVENTION

Figure 1:
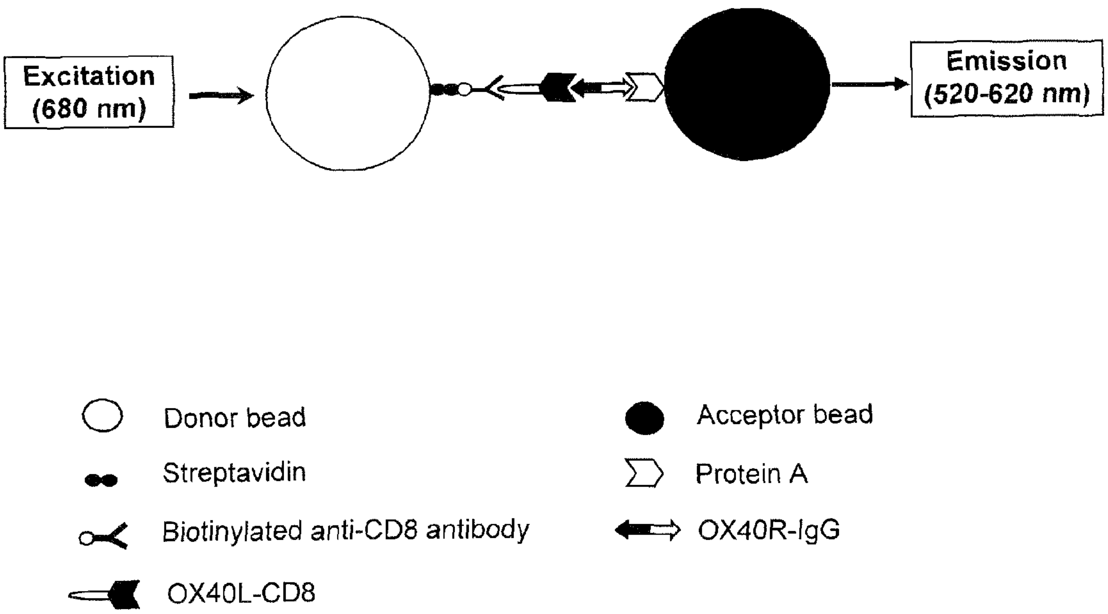
FIG. 1: experimental design of the Alphascreen™ assay initially developed for demonstrating the feasibility of this approach for studying OX40L-OX40R interaction.

In view of the evidences disclosed in the prior art, there is no indication of a specific peptide sequence into OX40L extracellular domain that would be useful as OX40R binding agent for inhibiting OX40R-OX40L interaction.

By screening series of peptides derived from OX40L extracellular domain, short amino acid sequences that interact with OX40R with high affinity and compete with OX40L, were surprisingly identified and characterized as inhibitors of OX40R-OX40L interaction.

Accordingly, the present invention discloses a novel OX40R binding agent which is the peptide sequence corresponding to amino acids 94-124 (P5; SEQ ID NO: 6) of human OX40L.

The present invention discloses OX40R binding agents which are peptide sequences of human OX40L consisting of a peptide sequence corresponding to amino acids 94-124 (peptide P5; SEQ ID NO: 6) wherein one or more amino acids have been deleted, and comprising amino acids 107-111 (peptide P5-1a; SEQ ID NO: 13) of human OX40L. In particular these peptides have between 5 and 10 amino acids, and, more in particular, have the sequence corresponding to amino acids 107-116 (peptide P5-1; SEQ NO ID: 8), or 107-111 (peptide P5-1a; SEQ ID NO: 13) of human OX40L.

The peptide P5, as well as the P5 fragments above defined, has been shown (or inferred) to bind human OX40R protein in the examples of the present patent application. This binding activity has been tested using in vitro assays employing recombinant forms of OX40L and OX40R, and demonstrating that OX40L can be effectively competed by the claimed peptide sequences, Novel means for inhibiting undesirable OX40R-OX40L interactions and cell signaling associated to human diseases are therefore provided by the present Invention.

Fragments of the extracellular domain of human ACT-4-L, which is an alternative name of OX40L, were disclosed as potential OX40R binding agents being associated to functional or structural domains in the extracellular domain of OX40L (WO 95/21915). However, no evidence has been provided in the literature on functional or structural domains of human OX40L corresponding to peptide P5, or to its fragments such as the peptides P5-1 and P5-1a, as having competing activities towards OX40L. Peptides designed on the mouse OX40L extracellular domain sequence have been used as antigens for generating anti-OX40L antibodies (Stuber E and Strober W, 1996), but, also in view of the limited conservation of mouse and human OX40L in this region (FIGS. 5A and 6A), it cannot be inferred that any of these sequences can efficiently compete human OX40L for the binding to human OX40R.

The present patent application successfully demonstrates that, even if no functional or structural domain can be inequivocally predicted by comparing other ligand-receptor pairs belonging to the same protein families (Bodmer J L et al., 2002), or by using well-known algorithms for protein structure prediction such as PREDATOR, PHD or HNN (accessible, for example, at http://npsa-pb ibcp.fr/cgi-bin/npsa_automat.pl?page=/NPSA/npsa_server.html), such peptides are surprisingly effective as OX40R binding agents capable of inhibiting OX40R-OX40L interaction.

The term "peptide" is ordinarily applied to a polypeptidic chain containing from 4 to 40 or more contiguous amino acids, usually from 4 to 20 contiguous amino acids. Such peptides can be generated by methods known to those skilled in the art, including partial proteolytic cleavage of a larger protein, chemical synthesis, or genetic engineering.

The term "active" defines the compound showing the OX40R binding properties demonstrated for the peptides of the present invention.

The properties of the peptide P5 and of its specific fragments exemplified by peptides P5-1 and P5-1a can be maintained, or even potentiated, in their active mutants. This category of molecules includes analogs of these sequences wherein one or more amino acid residues have been conservatively substituted, provided they display the same biological activity characterized in the present invention at comparable or even higher levels, as determined by means known in the art or disclosed in the Examples below.

In accordance with the present invention, preferred changes in these active mutants are commonly known as "conservative" or "safe" substitutions. Conservative amino acid substitutions are those with amino acids having sufficiently similar chemical properties, in order to preserve the structure and the biological function of the molecule. It is clear that insertions and deletions of amino acids may also be made in the above defined sequences without altering their function, particularly if the insertions or deletions only involve a few amino acids, e.g., under ten, and preferably under three, and do not remove or displace amino acids which are critical to the functional conformation of a protein or a peptide.

The literature provide many models on which the selection of conservative amino acids substitutions can be performed on the basis of statistical and physico-chemical studies on the sequence and/or the structure of natural protein (Rogov S I and Nekrasov A N, 2001). Protein design experiments have shown that the use of specific subsets of amino acids can produce foldable and active proteins, helping in the classification of amino acid "synonymous" substitutions which can be more easily accommodated in protein structure (Murphy L R et al., 2000). The synonymous amino acid groups and more preferred synonymous groups are those defined in Table I.

These alternative compounds are intended to comprehend molecules with changes to the selected sequences of human OX40L which do not affect the basic characteristics disclosed in the present patent application, particularly insofar as its ability of binding and inhibiting OX40R is concerned. Similar compounds may result from conventional site-directed mutagenesis technique of the encoding DNA, from combinatorial technologies at the level of encoding DNA sequence (such as DNA shuffling, phage display/selection) or of amino acids, from computer-aided design studies, or any other known technique suitable thereof, which provide a finite set of substantially corresponding mutated peptides which can be routinely obtained and tested by one of ordinary skill in the art using the teachings presented in the prior art and in the Examples of the present patent application.

The present patent application discloses novel OX40 binding agents being fusion polypeptides or peptides comprising the amino acid sequence P5, P5-1, P5-1a, or any of their active mutants as defined above, and an amino acid sequence belonging to a protein sequence other than human OX40L. This heterologous latter sequence should provide additional properties without considerably impairing OX40R binding activity. Examples of such additional properties are an easier purification procedure, a longer lasting half-life in body fluids, or extracellular localization. This latter feature is of particular importance for defining a specific group of fusion or chimeric proteins included in the above definition since it allows the peptides characterized as OX40R binding agent in this patent application to be localized in the space where not only where the isolation and purification of these peptides is facilitated, but also where OX40L and OX40R naturally interact.

Additional protein sequences which can be comprised in fusion proteins including the OX40R binding agent of the Invention can be chosen amongst membrane-bound proteins, extracellular domains of membrane-bound protein, immunoglobulin constant region, multimerization domains, extracellular proteins, signal peptide-containing proteins, export signal-containing proteins.

The choice of one or more of these sequences to be fused to the OX40 binding agent is functional to specific use of said agent. As a general procedure, these fusion proteins can be produced by generating nucleic acid segments encoding them, using common genetic engineering techniques, and cloning in replicable vector of viral or plasmid origin which are used to modify a Prokaryotic or Eukaryotic host cell, using episomal or non-/homologously integrated vectors, as well as transformation-, infection-, or transfection-based technologies. These vectors should allow the expression of the fusion protein including the OX40R binding agent in the prokaryotic or eukaryotic host cell under the control of their own transcriptional initiation/termination regulatory sequences, which are chosen to be constitutively active or inducible in said cell. A cell line substantially enriched in such cells can be then isolated to provide a stable cell line. In particular, whenever the cells modified to express the OX40R binding agents of the invention are directly used or administered, preferred cells are human cells normally expressing OX40L, in particular human B cells.

When the additional protein sequence, as in the case of the sequence of extracellular, export signal, or signal-peptide containing proteins, allows the OX40R binding domain to be secreted in the extracellular space, the agent can be more easily collected and purified from cultured cells in view of further processing or, alternatively, the cells can be directly used or administered.

When the additional protein, as in the case of the sequence of membrane-bound proteins, allows the immobilization of the OX40R binding agent on the surface of the cell, the agent can be less easily collected and purified from the cultured cells in view of further processing but the cells can be directly used or administered providing the agent in a form corresponding to the one of natural OX40L, possibly improving its properties.

Finally, since OX40L-OX40R interaction is known to involve multimerization of the proteins, in particular the trimerization (Al Shamkhani A et al., 1997). Therefore, the fusion protein may also include sequence allowing the multimerization of the resulting protein, such as the immunoglobulin constant regions, extracellular domains of membrane-bound proteins, or trimerization domains known in the art as being present in TNFR-like (WO 00/39295) or in other proteins (WO 01/49866, WO 99/10510, WO 01/98507). Other useful protein sequences that can be included are the ones providing means of purification by affinity chromatography (Constans A, 2002; Lowe C R et al., 2001).

The polypeptides and the peptides of the present invention can be in alternative forms which can be preferred according to the desired method of use and/or production, for example as active fractions, precursors, salts, or derivatives.

The term "fraction" refers to any fragment of the polypeptidic chain of the compound itself, alone or in combination with related molecules or residues bound to it, for example residues of sugars or phosphates, or aggregates of the original polypeptide or peptide. Such molecules can result also from other modifications which do not normally alter primary sequence, for example in vivo or in vitro chemical derivativization of peptides (acetylation or carboxylation), those made by modifying the pattern of phosphorylation (introduction of phosphotyrosine, phosphoserine, or phosphothreonine residues) or glycosylation (by exposing the peptide to enzymes which affect glycosylation e.g., mammalian glycosylating or deglycosylating enzymes) of a peptide during its synthesis and processing or in further processing steps. For example, P5 and P5-1 contain a potential glycosylation site (amino acids 114-116 in human OX40L) and this can be modified accordingly during the recombinant expression in the host cell or during chemical synthesis.

The "precursors" are compounds which can be converted into the compounds of present invention by metabolic and enzymatic processing prior or after the administration to the cells or to the body.

The term "salts" herein refers to both salts of carboxyl groups and to acid addition salts of amino groups of the peptides, polypeptides, or analogs thereof, of the present invention. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Any of such salts should have substantially similar activity to the peptides and polypeptides of the invention or their analogs.

The term "derivatives" as herein used refers to derivatives which can be prepared from the functional groups present on the lateral chains of the amino acid moieties or on the N-/ or C-terminal groups according to known methods. Such derivatives include for example esters or aliphatic amides of the carboxyl-groups and N-acyl derivatives of free amino groups or O-acyl derivatives of free hydroxyl-groups and are formed with acyl-groups as for example alcanoyl- or aroyl-groups.

Another object of the present invention are novel OX40R binding agents consisting of peptide mimetics (also called peptidomimetics) of the peptides P5, its specific fragments exemplified by peptides P5-1 and p5-1a, the corresponding active mutants as defined above, in which the nature of peptide or polypeptide has been chemically modified at the level of amino acid side chains, amino acid chirality, and/or peptide backbone. These alterations are intended to provide OX40R binding agents having similar (if not improved) therapeutic, diagnostic and/or pharmacokinetic properties.

For example, when the peptide is susceptible to cleavage by peptidases following injection into the subject is a problem, replacement of a particularly sensitive peptide bond with a non-cleavable peptide mimetic can provide a peptide more stable and thus more useful as a therapeutic. Similarly, the replacement of an L-amino acid residue is a standard way of rendering the peptide less sensitive to proteolysis, and finally more similar to organic compounds other than peptides. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl. Many other modifications providing increased potency, prolonged activity, easiness of purification, and/or increased half-life are known in the art (WO 02/10195; Villain M et al., 2001). Preferred alternative, "synonymous" groups for amino acids included in peptide mimetics are those defined in Table II.

The techniques for the synthesis and the development of peptide mimetics, as well as non-peptide mimetics, are well known in the art (Sawyer T K, 1997; Hruby V J and Balse P M, 2000; Golebiowski A et al., 2001; Kim H O and Kahn M, 2000). Various methodology for incorporating unnatural amino acids into proteins, using both in vitro and in vivo translation systems, to probe and/or improve protein structure and function are also disclosed in the literature (Dougherty D A, 2000).

Novel OX40R binding agents can be peptides, peptide mimetics, or non-peptide mimetics identified by methods of computer-aided drug design which make use of the structure and/or sequence of the peptides P5, its specific fragments exemplified by peptides P5-1 and P5-1a, or the corresponding active mutants as defined above. The tridimensional structures of OX40L and OX40R, as separate molecules or as a complex, have not been solved yet but the disclosure provided in this patent application, once that this information will be available, will allow to study the interaction between OX40L and OX40R with greater efficacy using these and other simulation technologies (Cochran A et al., 2001; Kraemer-Pecore C M et al., 2001). Such computer-assisted analysis can be exploited to develop improved peptide or non-peptide mimetic drugs in the form of synthetic organic molecules or peptides (for example, having between 4 and 20 amino acid). Once that these compounds have been screened and found to be capable of binding OX40R and competing with OX40L, it will then be assessed their utility using cell or animal models.

Useful conjugates or complexes of the OX40R binding agents of the present invention can be generated, using molecules and methods known in the art (as shown for anti-OX40R antibodies in WO 95/21251) to improve their detection (with radioactive or fluorescent labels, biotin), their therapeutic efficacy (with cytotoxic agents), and/or their delivery, with polyethylene glycol and other natural or synthetic polymers (Pillai O and Panchagnula R, 2001).

The peptides P5, its specific fragments exemplified by peptides P5-1 and P5-1a, the corresponding active mutants, and the fusion proteins containing them, can be prepared by known chemical synthesis or by recombinant DNA-based techniques.

Another object of the invention are the nucleic acids encoding for the OX40R binding agents of the invention, including nucleotide sequences substantially the same.

"Nucleotide sequences substantially the same" includes all other nucleic acid sequences that, by virtue of the degeneracy of the genetic code, also code for the given amino acid sequences.

The invention also includes vectors of viral or plasmid origin which allows the expression of the nucleic acid encoding for the OX40R binding agents of the Invention and prokaryotic or eukaryotic host cells transformed with such vectors. A stable cell line substantially enriched in these transformed cells can be isolated, also on the basis of the expression features of the OX40R binding agent, which can be secreted or expressed on the membrane surface, for example on human B cells.

OX40R binding agents of the invention can be produced by method wherein the host cells above described, are cultured in an appropriate culture media and the OX40R binding agent is collected.

The DNA sequence coding for the proteins of the invention can be inserted and ligated into a suitable vector. Once formed, the expression vector is introduced into a suitable host cell, which then expresses the vector(s) to yield the desired protein.

Expression of any of the recombinant proteins of the invention as mentioned herein can be effected in eukaryotic cells (e.g. yeasts, insect or mammalian cells) or prokaryotic cells, using the appropriate expression vectors. Any method known in the art can be employed.

For example the DNA molecules coding for the proteins obtained by any of the above methods are inserted into appropriately constructed expression vectors by techniques well known in the art. Double stranded cDNA is linked to plasmid vectors by homopolymeric tailing or by restriction linking involving the use of synthetic DNA linkers or blunt-ended ligation techniques: DNA ligases are used to join the DNA molecules, and undesirable joining is avoided by treatment with alkaline phosphatase.

In order to be capable of expressing the desired protein, an expression vector should also comprise specific nucleotide sequences containing transcriptional and translational regulatory information linked to the DNA coding the desired protein in such a way as to permit gene expression and production of the protein. First in order for the gene to be transcribed, it must be preceded by a promoter recognizable by RNA polymerase, to which the polymerase binds and thus initiates the transcription process. There are a variety of such promoters in use, which work with different efficiencies (strong and weak promoters).

For Eukaryotic hosts, different transcriptional and translational regulatory sequences may be employed, depending on the nature of the host. They may be derived form viral sources, such as adenovirus, bovine papilloma virus, Simian virus or the like, where the regulatory signals are associated with a particular gene which has a high level of expression. Examples are the T K promoter of the Herpes virus, the SV40 early promoter, the yeast gal4 gene promoter, etc. Transcriptional initiation regulatory signals may be selected which allow for repression and activation, so that expression of the genes can be modulated.

The DNA molecule comprising the nucleotide sequence coding for the protein of the invention is inserted into vector(s), having the operably linked transcriptional and translational regulatory signals, which is capable of integrating the desired gene sequences into the host cell.

The cells that have been stably transformed by the introduced DNA can be selected by also introducing one or more markers allowing for selection of host cells containing the expression vector. The marker may also provide for phototrophy to an auxotropic host, biocide resistance, e.g. antibiotics, or heavy metals such as copper, or the like. The selectable marker gene can either be directly linked to the DNA gene sequences to be expressed, or introduced into the same cell by co-transfection.

Additional elements of the vectors may also be useful for obtaining an optimal production of proteins of the invention, in particular for selecting a particular cell containing plasmid or viral vector: the ease with which recipient cells, that contain the vector may be recognized and selected from those recipient cells which do not contain the vector; the number of copies of the vector which are desired in a particular host; and whether it is desirable to be able to "shuttle" the vector between host cells of different species.

Once the vector(s) or DNA sequence containing the construct(s) has been prepared for expression the DNA construct(s) may be introduced into an appropriate host cell by any of a variety of suitable means: transformation, transfection, conjugation, protoplast fusion, electroporation, calcium phosphate-precipitation, direct microinjection, etc.

Host cells may be either prokaryotic or eukaryotic. Preferred are eukaryotic hosts, e.g. mammalian cells, such as human, monkey, mouse, and Chinese Hamster Ovary (CHO) cells, because they provide post-translational modifications to protein molecules, including correct folding or glycosylation at correct sites. Also yeast cells can carry out post-translational peptide modifications including glycosylation. A number of recombinant DNA strategies exist which utilize strong promoter sequences and high copy number of plasmids that can be utilized for production of the desired proteins in yeast. Yeast recognizes leader sequences on cloned mammalian gene products and secretes peptides bearing leader sequences (i.e., pre-peptides).

After the introduction of the vector(s), the host cells are grown in a selective medium, which selects for the growth of vector-containing cells. Expression of the cloned gene sequence(s) results in the production of the desired proteins.

These objects of the invention can be achieved by combining the disclosure provided by the present patent application on recombinant OX40R binding agents, with the knowledge of common molecular biology techniques. Many reviews (Makrides S C, 1999) and books provides teachings on how to clone and produce recombinant proteins using vectors and Prokaryotic or Eukaryotic host cells, such as some titles in the series "A Practical Approach" published by Oxford University Press ("DNA Cloning 2: Expression Systems", 1995; "DNA Cloning 4: Mammalian Systems", 1996; "Protein Expression", 1999; "Protein Purification Techniques", 2001).

Examples of chemical synthesis technologies, which are more indicated for producing the OX40R binding agent of the Invention when they are in the form of peptide or peptide mimetics, are solid phase synthesis and liquid phase synthesis. As a solid phase synthesis, for example, the amino acid corresponding to the C-terminus of the peptide to be synthetized is bound to a support which is insoluble in organic solvents, and by alternate repetition of reactions, one wherein amino acids with their amino groups and side chain functional groups protected with appropriate protective groups are condensed one by one in order from the C-terminus to the N-terminus, and one where the amino acids bound to the resin or the protective group of the amino groups of the peptides are released, the peptide chain is thus extended in this manner.

Solid phase synthesis methods are largely classified by the tBoc method and the Fmoc method, depending on the type of protective group used. Typically used protective groups include tBoc (t-butoxycarbonyl), Cl-Z (2-chlorobenzyloxycarbonyl), Br-Z (2-bromobenzyloxycarbonyl), Bzl (benzyl), Fmoc (9-fluorenylmethoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and C12-Bzl (2,6-dichlorobenzyl) for the amino groups; NO2 (nitro) and Pmc (2,2,5,7,8-pentamethylchromane-6-sulphonyl) for the guanidino groups); and tBu (t-butyl) for the hydroxyl groups). After synthesis of the desired peptide, it is subjected to the de-protection reaction and cut out from the solid support. Such peptide cutting reaction may be carried with hydrogen fluoride or tri-fluoromethane sulfonic acid for the Boc method, and with TFA for the Fmoc method.

The OX40R binding agents obtained by recombinant DNA or chemical synthesis technologies are finally subjected to one or more steps of purification. Purification can be carried out by any one of the methods known for this purpose, i.e. any conventional procedure involving extraction, precipitation, chromatography, electrophoresis, or the like. For example, HPLC (High Performance Liquid Chromatography) can be used. The elution can be carried using a water-acetonitrile-based solvent commonly employed for protein purification. The invention includes purified preparations of the OX40R binding agents of the invention. Purified preparations, as used herein, refers to the preparations which are at least 1%, preferably at least 5%, by dry weight of the compounds of the invention.

The compounds of the invention described above (proteins, peptides, organic compounds) can be as a medicament, being antagonists of human OX40L, and in view of the literature on the activity of OX40L as inducer of RANTES expression (Kotani A. et al., 2002), and antagonists of human RANTES.

The OX40R binding agents of the invention can be used as active ingredient in pharmaceutical compositions for the prophylaxis and/or treatment of autoimmune diseases, inflammation, or infection.

OX40R binding agent of the invention, once bound to OX40R, acts as antagonist of OX40L, the therapeutical potential of such molecule is in the prophylaxis and/or treatment of autoimmune diseases (e.g. inflammatory bowel disease, rheumatoid arthritis, and multiple sclerosis), inflammations or infections, where an inhibition of CD4" T cells activation is beneficial. This latter effect can be also used for reducing the population of CD4' T cells that express OX40R.

The present invention also provides pharmaceutical compositions for the prophylaxis and/or treatment of diseases related to $CD4^+$ T cells, comprising one of the OX40R binding agents of the invention as active ingredient. These pharmaceutical compositions can be formulated in combination with pharmaceutically acceptable carriers, excipients, stabilizers, or diluents. Depending on the properties of the agent, the pharmaceutical composition can be useful for diseases related to $CD4^+$ T cells such as autoimmune diseases, inflammations, or infections.

Pharmaceutical compositions comprising the OX40R binding agents of the present invention include all compositions wherein said compound is contained in therapeutically effective amount, that is, an amount effective to achieve the medically desirable result in the treated animal. The pharmaceutical compositions may contain suitable pharmaceutically acceptable carriers, biologically compatible vehicles suitable for administration to an animal (for example, physiological saline) and eventually comprising auxiliaries (like excipients, stabilizers or diluents) which facilitate the processing of the active compounds into preparations which can be used pharmaceutically.

The pharmaceutical compositions may be formulated in any acceptable way to meet the needs of the mode of administration. The use of biomaterials and other polymers for drug delivery, as well the different techniques and models to validate a specific mode of administration, are disclosed in literature (Luo B and Prestwich G D, 2001; Cleland J L et al., 2001). Modifications of the compounds of the invention to improve penetration of the blood-brain barrier would also be useful. Other methods of biomimetic transport and rational drug delivery in the field of transvascular drug delivery are known in the art (Ranney D F, 2000).

Any accepted mode of administration can be used and determined by those skilled in the art. For example, administration may be by various parenteral routes such as subcutaneous, intravenous, intradermal, intramuscular, intraperitoneal, intranasal, transdermal, oral, or buccal routes. Parenteral administration can be by bolus injection or by gradual perfusion over time. Preparations for parenteral administration include sterile aqueous or non-aqueous solutions, suspensions, and emulsions, which may contain auxiliary agents or excipients known in the art, and can be prepared according to routine methods. In addition, suspension of the active compounds as appropriate oily injection suspensions may be administered. Suitable lipophilic solvents or vehicles include fatty oils, for example, sesame oil, or synthetic fatty acid esters, for example, sesame oil, or synthetic fatty acid esters, for example, ethyl oleate or triglycerides. Aqueous injection suspensions that may contain substances increasing the viscosity of the suspension include, for example, sodium carboxymethyl cellulose, sorbitol, and/or dextran. Optionally, the suspension may also contain stabilizers. Pharmaceutical compositions include suitable solutions for administration by injection, and contain from about 0.01 to 99 percent, preferably from about 20 to 75 percent of active compound together with the excipient. Compositions which can be administered rectally include suppositories.

It is understood that the dosage administered will be dependent upon the age, sex, health, and weight of the recipient, kind of concurrent treatment, if any, frequency of treatment, and the nature of the effect desired. The dosage will be tailored to the individual subject, as is understood and determinable by one of skill in the art. The total dose required for each treatment may be administered by multiple doses or in a single dose. The pharmaceutical composition of the present invention may be administered alone or in conjunction with other therapeutics directed to the condition, or directed to other symptoms of the condition. Usually a daily dosage of active ingredient is comprised between 0.01 to 100 milligrams per kilogram of body weight.

The compounds of the present invention may be administered to the patient intravenously in a pharmaceutically acceptable carrier such as physiological saline. Standard methods for intracellular delivery of peptides can be used, e.g. delivery via liposomes. Such methods are well known to those of ordinary skill in the art. The formulations of this invention are useful for parenteral administration, such as intravenous, subcutaneous, intramuscular, and intraperitoneal.

As well known in the medical arts, dosages for any one patient depends upon many factors, including the patients size, body surface area, age, the particular compound to be administered, sex, time and route of administration, general health, and other drugs being administered concurrently.

The OX40R binding agents of the present Invention can be used for the detection of the extracellular domain of OX40R protein, as membrane-bound or a soluble protein. Obviously this use can be extended to the detection of activated $CD4^+$ T cells expressing OX40R protein.

The method of detections based on these uses comprises a first step in which a sample is contacted with the agents or the cells, and a second step in which the interaction between the extracellular domain of OX40R protein is detected directly (by the means of any label associated to the agent or the cell, as described before) or indirectly (by the means of the effects of this binding on the OX40R protein or the OX40R-expressing cell, for example), in order to indicate the presence of these elements.

The agent or the cells can be immobilized, before or after being put in contact with the sample, onto supports which allow not only the detection but also the purification, and/or the concentration of the OX40R extracellular domain, as membrane-bound or a soluble protein, or OX40R-expressing cells. These supports can be consequently used in methods for the detection, the purification, and/or the concentration of OX40R extracellular domain, as membrane-bound or a soluble protein, or OX40R-expressing cells in a sample by contacting said sample with the supports, or with cells expressing the OX40R binding agent of the present invention. This and the previously described detection methods can be used to diagnose a condition associated to decreased or increased presence of $CD4^+$ T cells or of soluble OX40R protein.

The OX40R binding agent of the present invention, or the cells expressing them, can be administered in methods for the prophylaxis and/or treatment of autoimmune diseases, inflammations, or infections.

The present invention also discloses screening assay for the determination of the nature and the activity of compounds, as provided in Examples of the present patent application, inhibiting OX40R-OX40L interactions comprising:

a) Forming a sample comprising the following elements:

i. An element constituting the OX40R binding agent, chosen amongst the compounds, the cells, and the supports described in the present invention;

ii. An element constituting the OX40R moiety, chosen amongst a protein comprising the extracellular domain of OX40R, a cell line expressing OX40R extracellular domain on its surface, and a cell line secreting extracellular domain of OX40R; and iii. The compound(s) to be tested as inihibitor(s) of OX40R-OX40L interaction.

b) Detecting, directly or indirectly, the effect of the compounds (iii) on the interactions between the elements (i) and (ii).

c) Comparing the effect detected in (b) amongst samples different in terms of quality and/or quantity of the elements of (a).

The support disclosed above represents a preferable element since those kinds of screening are more efficient and quick by using an binding element immobilized on supports like plastic microtiter plate or beads.

The present invention also provides novel kits comprising the OX40R binding agents, cells expressing them, or supports comprising them, for detecting extracellular domain of OX40R protein (as membrane-bound or a soluble protein) or activated $CD4^+$ T cells, allowing also the diagnosis of a condition due to a decreased or increased presence of $CD4^+$ T cells or of soluble OX40R protein in a sample obtained from a patient.

Finally, the present invention also provides a kit for screening compounds inhibiting the interaction of a protein ligand with a membrane-associated protein, comprising the extracellular portion of the membrane-associated protein and the protein ligand as fusion proteins having different tag sequences.

All references cited herein are entirely incorporated by reference herein, including all data, tables, figures, and text presented in the cited references. Additionally, the entire contents of the references cited within the references cited herein are also entirely incorporated by reference. Reference to known method steps, conventional method steps, known methods or conventional methods is not in any way an admission that any aspect, description or embodiment of the present invention is disclosed, taught or suggested in the relevant art.

Once understood the features of the methods and products disclosed in present application, the necessity and kind of additional steps can be easily deduced by reviewing prior art, as well as the non-limiting following figures and examples describing the basic details and some applications of the invention.

EXAMPLES

Example 1

Experimental Design for Detecting OX4014-OX40R Interactions Using an AlphaScreen™-Based Competition Assay Methods Proteins Human OX40R-IgG1 fusion protein has been described previously (Godfrey et al., 1994). The recombinant protein was prepared by constructing a mammalian expression vector based on pCEP4 (Invitrogen) in which the cDNA encoding for the extracellular portion of human OX40R (amino acids 1-208 of SWISSPROT Acc. No P43489) was in-frame fused to the 5' end of the cDNA encoding for the constant region of human $IgG_1$ (hinge region, CH2 and CH3; amino acids 98-330 of SWISSPROT Acc. No P01857). Recombinant OX40R-IgG1 is expressed as a secreted protein due to the signal sequence of OX40R.

HEK293-EBNA cells were transfected, using the calcium phosphate technique with the expression construct, which contains a selectable marker gene for Hygromycin. Cells were seeded at a density of $2\times10^5$ cells/ml in growth medium (DMEM/F-12 (1:1) supplemented with 10% Fetal Bovine Serum and 4 mM L-glutamine; Sigma Chemicals). The following day, the medium was replaced by DMEM/F-12 (1:1) supplemented with 2% Fetal Bovine Serum and 4 mM L-glutamine. One hour later, cells were transfected and incubated at 37° C. in a humidified atmosphere containing 5% $CO_2$ for 4 hours, then medium was changed back to the growth medium containing 10% Fetal Bovine Serum. Two days post transfection, the selection agent (Hygromycin B; 300 μg/ml) was added to the medium. A clone correctly expressing OX40R-IgG1 was isolated amongst the selected cells.

Recombinant OX40R-IgG was purified from the supernatant of a cell culture generated from the isolated clone. The supernatant was clarified by centrifugation (10 minutes at 500×g) and subsequently filtered using PVDF membranes of 0.45 and 0.22 micrometrs pore size (Millipore). In parallel, the purification column, containing 38 ml resin on which recombinant protein G was immobilized (Pharmacia), was equilibrated in loading buffer (0.1 M Tris, pH 7.0) using a Bio-Logic FPLC system (Biorad). After equilibration with 20 column-volumes (CV) of loading buffer, the sample was applied to the column at a flow rate of 1 ml/min. The column was washed away with a 10 CV of loading buffer to eliminate protein bound non-specifically to the resin. OX40R-IgG1 fusion protein, immobilized on the protein G via the IgG1 moiety, was eluted by a step gradient using a 0.1 Glycine/HCl (pH 3.0) elution buffer. The resulting fractions were directly neutralized with 1M Tris (pH 7.6) to prevent protein degradation in the acidic elution buffer. Finally, the fractions containing the OX40R—IgG1 fusion protein were desalted using a Sephadex G25 column (Pharmacia) equilibrated in PBS (Phosphate Buffer Saline) and stored in aliquots at ±80° C. until being used for the assays.

Human OX40L-murine CD8 and anti-murine CD8 biotinylated antibodies are commercially available (Ancell), as well as Suramin (Sigma Chemicals). Recombinant human soluble OX40L was prepared as a fusion protein with Glutathione-S-Transferase (GST) in a Baculovirus Expression System (Gateway™, Invitrogen) by cloning the extracellular portion of OX40L fused to GST in a plasmid that was then used to transfect SF9 cells. Expression and purification were performed according to Manufacturer's instructions.

Alphascreen™ Assay

Alphascreen™ modified acceptor and donor beads were purchased (Biosignal Packard). OX40R-IgG1 and OX40L-CD8 fusion proteins were immobilized, respectively, onto protein A-conjugated acceptor beads and, by the means of a biotinylated anti-CD8 antibody, onto streptavidin-conjugated donor beads.

The binding assay was performed using Costar® 384-well white polystyrene plates (Corning). Each well of a 384-well plate contained a reaction mix having a volume of 25 microliters. Each of the five components of the reaction mix (OX40R-IgG1, OX40L-CD8, biotinylated anti-CD8, streptavidin-conjugated donor beads, and Protein A-conjugated acceptor beads) was added in a volume of 5 microliters. All dilutions were made in assay buffer (Phosphate Buffer Saline and 0.1% BSA), with or without dimethyl sulfoxide (DMSO).

In the standard assay, OX40-IgG1 and OX40L-CD8 were incubated together for 30 minutes, and then biotinylated anti-CD8 antibody (10 nM) was added. Following another incubation period of 30 minutes, streptavidin donor beads (20 μg/ml) and Protein A acceptor beads (20 μg/ml) were added to each individual well. The plate was counted 1 hour later using a Packard Fusion™ reader (Biosignal Packard) set at a read time of 1 second/well. Owing to the light sensitivity of the donor and acceptor beads, the experiments were carried out under blue light and all incubation periods were performed at room temperature. The plate was read at an excitation wavelength of 680 nanometers combined with a shorter emission wavelength of 520-620 nanometers.

Data Analyses

All $K_D$, $IC_{50}$ and $EC_{50}$ values were calculated using Prism® software (Graphpad Software). The transformation of $IC_{50}$ values into $K_i$ values was performed using the Cheng-Prusoff equation (Cheng Y C and Prusoff W H, 1973).

Results

OX40L binding assays known in the literature include FACS-based analysis (Taylor L et al, 2002), or a Biacore™-based analysis (Al-Shamkhani A et al., 1997). Being these techniques unsuitable for high throughput screenings, a more efficient system to establish the potential inhibiting properties of OX40L-derived peptides on the OX40R-OX40L interaction was set up by making use of a commercially available technology called Amplified Luminescent Proximity Homogeneous Assay Screen (Alphascreen™; Packard Bioscience), a method based on the Luminescent Oxygen Channeling Immunoassay (LOCI; EP515194; Ullman E et al., 1994).

Briefly, AlphaScreen™ technology provides an easy and reliable determination of the effect of compounds on biomolecular interactions and activities, in particular for protein/protein interaction assays. AlphaScreen™ relies on the use of "Donor" and "Acceptor" polystyrene beads, each coated with a layer of hydrogel providing functional groups for conjugation of a specific molecule. When a biological interaction between the immobilized molecules brings the beads into proximity, a cascade of chemical reactions is initiated to produce a greatly amplified signal. Upon laser excitation at 680 nanometers, a photosensitizer in the "Donor" bead converts ambient oxygen to a more excited singlet state. The excited singlet state oxygen molecules diffuse across a maximum distance of 200 nanometers before rapidly decaying. If an acceptor bead is in close proximity, these oxygen molecules react with a chemiluminescer (such as thioxene derivatives) contained in the acceptor beads to generate chemiluminescence. The activated fluorophores subsequently emit light at 520-620 nanometers. In the absence of a specific biological interaction, the singlet state oxygen molecules produced by the donor bead go undetected without the close proximity of the Acceptor bead. AlphaScreen™ technology allows the detection of interactions with affinities in the sub-nanomolar/micromolar range.

In the present case, the experimental set-up was first tested using only the basic binding partners, immobilized on Alphascreen™ beads by making use of different affinity tags having a short biological linker that avoids the use of exogenous labeling groups. The signal should be detected only when streptavidin donor and Protein A acceptor beads are separated by a distance of less than 200 nm, by virtue of the complex formed by biotinylated anti-CD8 antibody OX40L-CD8, and OX40R-IgG1 (FIG. 1). The IgG1-tagged extracellular domain of OX40R was incubated with soluble OX40L-CD8, forming a complex. Owing to the relevant tags, this complex was able to couple to Protein A acceptor beads and, in the presence of a biotinylated anti-CD8 antibody, and to the streptavidin donor beads, generating an detectable Alphascreen™ signal. In the presence of a compound competing for the OX40L-OX40R interaction, the donor and acceptor beads should no longer be in proximity and the signal should no longer be detected.

In the initial experiments performed to determine the feasibility of this assay, the Alphascreen™ signal was increased with the addition of OX40R-IgG1 in a dose-dependent manner (FIG. 2A). The calculated $EC_{50}$ values ($-\log EC_{50} \pm$SEM, Standard Error of the Mean) were $7.7\times10^{-9}$ M (8.11±0.04) and $7.9\times10^{-9}$ M (8.10±0.01) using 5 or 10 nM OX40-IgG1, respectively. The experiment was then repeated using a wider range of receptor concentrations (2.5-80 nM) in order to determine the optimal concentration to use for this binding assay. Seven concentrations were tested in total and results demonstrated that each concentration generated a dose-dependent increase of the Signal/Background (S/B) ratio in the Alphascreen™ signal following incubation with OX40L-CD8 (FIG. 2B). In all cases, there were no significant differences between the calculated $EC_{50}$ values, which remain in the nanomolar range.

Taking these results into account, further experiments were performed at a concentration of OX40R-IgG1 (10 nM) and of OX40L-CD8 (40 nM) allowing a good S/B window to work with and also ensured that the assay would be cost-effective by using only a minimum concentration of these fusion proteins.

Figure 3:
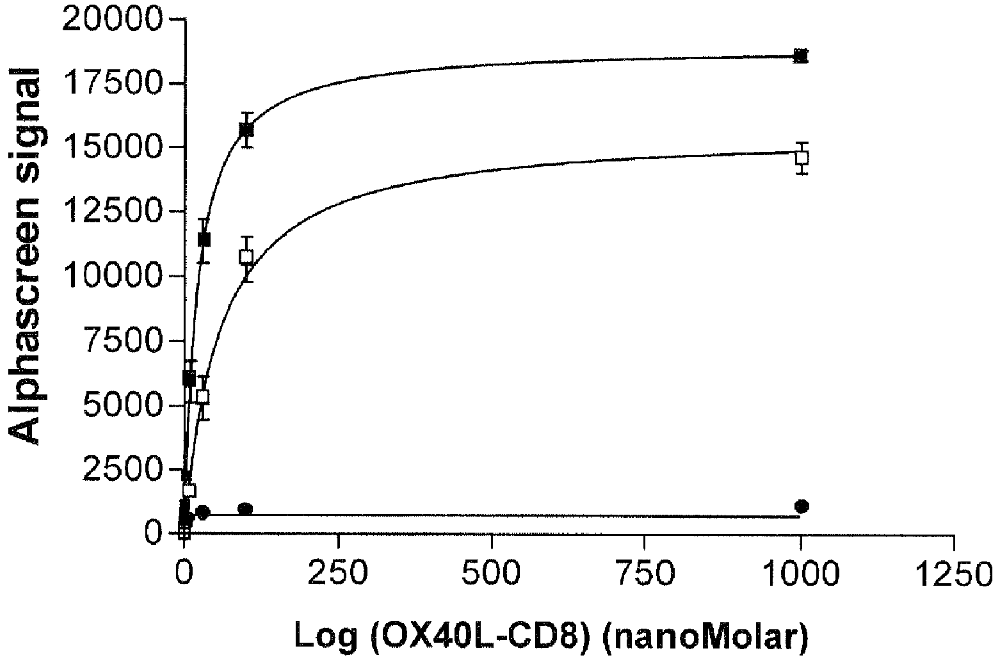
FIG. 3: $K_D$ determination of OX40L-CD8 for OX40R-IgG1. OX40R-IgG1 (10 nM) was incubated in the presence of increasing concentrations of OX40L-CD8. Specific binding (□) was calculated as the difference between total binding (■) and non-specific binding (●) determined in the presence of Suramin (1 mM). Data are expressed as mean±SEM from 3 experiments performed in triplicate.

The $K_D$ of OX40L-CD8 for OX40R-IgG1 was then calculated by subtracting the signal due to non-specific binding, as determined in the presence of suramin (1 mM), a small molecule inhibiting the interactions TNF-like proteins with their receptors (Alzani R et al., 1995). Specific binding of OX40L-CD8 was saturable and of high affinity (FIG. 3), with a calculated $K_D$ value of 20.7±5.2 nM. This is in agreement with literature values when binding affinity of OX40L-CD4 for OX40R was measured using a Biacore sensor chip method (Al Shamkhani A et al., 1997) and, in general, similar to $K_D$ values obtained for other members of the TNF receptor family for their respective ligands.

Figure 4:
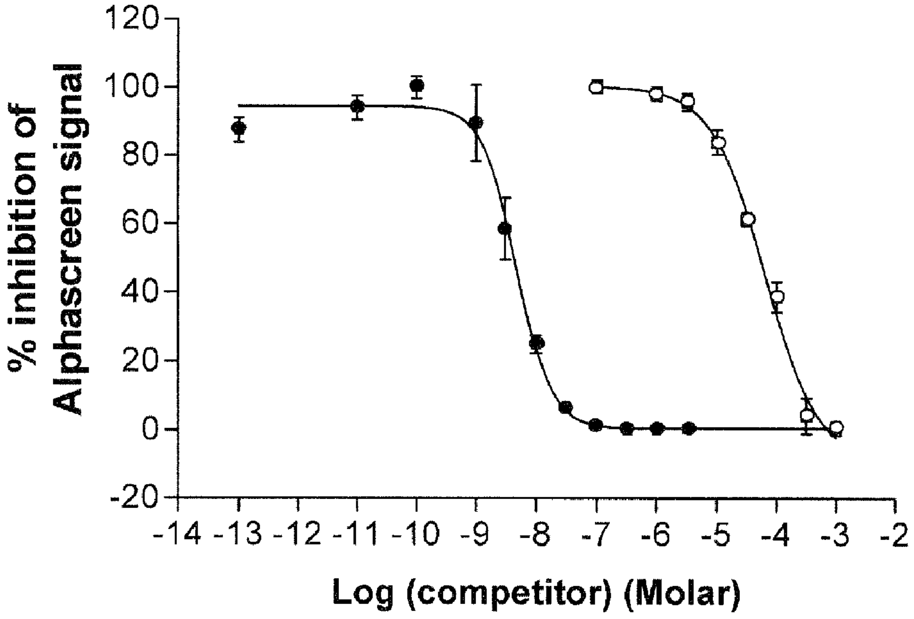
FIG. 4: Competition for OX40L-CD8 binding by OX40L and suramin. OX40-IgG (10 nM), OX40L-CD8 (40 nM) and increasing concentrations of soluble OX40L (●) or suramin (○) were incubated for 30 minutes prior to the addition of biotinylated anti-CD8 antibody (10 nM). Thirty minutes later streptavidin donor and protein A acceptor beads were added. The graph represents the percentage inhibition of the maximal Alphascreen™ signal (obtained in the absence of any inhibitor). Data are expressed as mean±SEM from 3 experiments performed in triplicate

The ability of two known competitors of OX40L-OX40R interactions (untagged recombinant human soluble OX40L and suramin), which are themselves unable to generate an Alphascreen™ signal in this assay in absence of OX40L-CD8, to displace OX40L-CD8 from OX40R-IgG1 was investigated. The displacement experiments were performed, taking into consideration the approximate $K_D$ value, with a concentration of OX40L-CD8 (40 nM) that was 4 times greater than that of the OX40R-IgG1 (10 nM). Increasing concentrations of OX40L (3 μM-0.1 pM) or suramin (1 mM±1 nM) were added to a reaction mixture also containing OX40-IgG1 (10 nM) and OX40L-CD8 (40 nM). Both compounds compete for OX40L-CD8 binding in a dose-dependent manner, with resulting $IC_{50}$ values (−log $IC_{50}$±SEM) of $5.9\times10^{-9}$ M (8.23±0.35) and $7.9\times10^{-5}$ M (4.10±0.06), respectively (FIG. 4). These values can be transformed by the Cheng-Prusoff equation (Cheng, Y C and Prusoff, W H, 1973) to $K_i$ values of 2.0 nM for OX40L and 26.3 μM for suramin. This latter value for suramin is similar to reported values for inhibition of TNF-α binding to the TNF receptor (Gray P W et al., 1990).

Further optimization of the assay was made to better define the conditions for performing the assay. The assay was able to tolerate, without any loss in signal, a dimethyl sulfoxide (DMSO) concentration up to 1%. The assay can be performed efficiently by combining OX40-IgG1, OX40L-CD8 and biotinylated anti-CD8 antibody into a first addition step, and combining streptavidin donor and Protein A acceptor beads in a second addition step, keeping a total incubation time of 60 minutes. Both mixtures can be prepared in advance to addition to the plate.

The Alphascreen™ technology above described, initially developed for detecting OX40L-derived peptide that competitively inhibited OX40L-OX40R interaction, would be suitable to screen also for any other selective small-molecule or peptide inhibitors of such interaction. Since this assay is homogeneous, highly sensitive, robust and suitable for automation in a 384-well format, the same approach is potentially adaptable to the development of biochemical screens for many other protein ligands that interact with membrane-associated proteins, simply by expressing the extracellular portion of the membrane-associated protein and the protein ligand as fusion proteins fusion protein with different tag sequence (IgG1 and CD8, respectively, in the present case).

Example 2

Identification of OX40L-Derived Peptides Binding OX40R

Methods

Peptides

Peptides (10-31 amino acids) were synthesized at purity ranging between 85-97% by Epytop (France), and stored in lyophilized form at −20° C. The peptides were solubilised in 0.1 mM NaOH in PBS before use. The name, sequence, and the corresponding amino acids in human OX40L for each peptide is shown in Table III.

Alphascreen™-Based Competition Assay

The soluble components (OX40-IgG1, OX40L-CD8 and biotinylated anti-CD8 antibody) were mixed at the concentration described before for the competition assays with OX40L and suramin (FIG. 4), together with various concentrations of each peptide in a 5 microliter volume into a first addition step. The streptavidin donor and Protein A acceptor beads were added 30 minutes later. The plates were incubated for 2 hours in the dark, at room temperature and with shaking, before reading at a long excitation wavelength of 680 nm combined with a shorter emission wavelength of 520-620 nanometers, as described in Example 1.

Fluorescence Quenching Assay

The fluorescence quenching assay was performed as previously described (Golabek A et al., 2000). OX40R-IgG1 (35 micrograms) was dissolved in 500 microliters of PBS and the fluorescence spectum was recorded at 295-420 nanometers with an excitation wavelength of 290 nanometers using a spectrofluorimeter (Perkin Elmer LS50B) with the slits set at 5 nanometers. Fluorescence spectra of human OX40R-IgG1 were then recorded in the presence of increasing concentrations (5-1000 nM) of P5 and P5-1 peptides after 15 minutes of equilibration. The fluorescence change at 336 nanometers was plotted versus peptide concentration and the resulting curves were analyzed by nonlinear regression fit with Prism® software (GraphPad).

Results

A series of partially overlapping peptides were designed on the sequence of extracellular domain of human OX40L (FIG. 5A; Table III), which corresponds to the amino acids 51-183 of the protein. In this area, two peptides were previously designed on the sequence of mouse OX40L for raising anti-OX40L antibodies (Stuber E and Strober W, 1996).

Using a first series of peptides in the Alphascreen™-based competition assay described in Example 1, it was possible to define a peptide (P5) capable to inhibit the binding of OX40R to OX40L in the micromolar range (FIG. 5B), an affinity value which is pharmacologically relevant.

Figure 6:
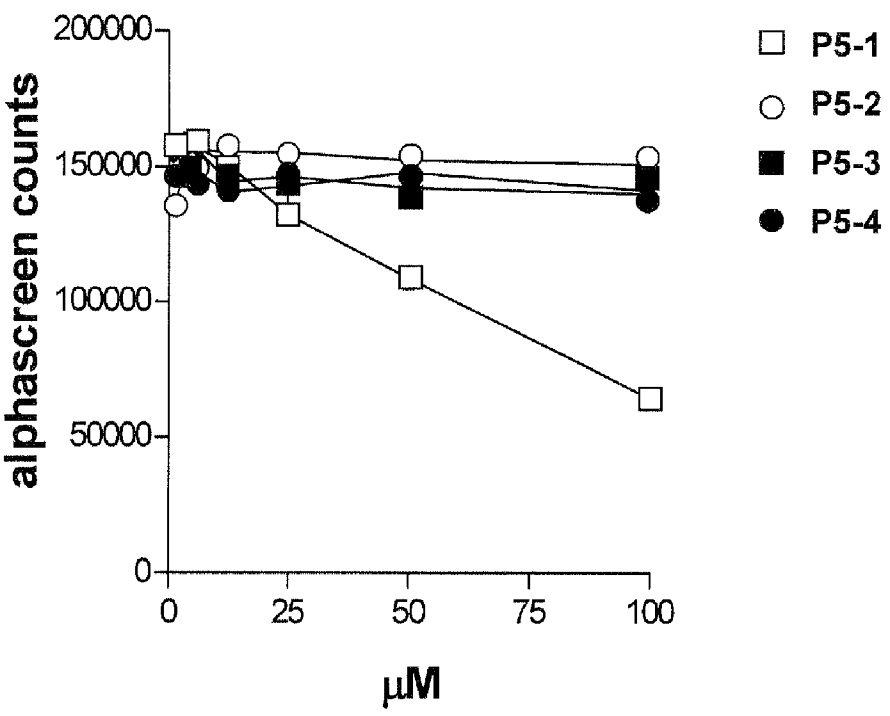
FIG. 6: binding of P5-derived peptides (SEQ ID NOs: 6 and 8-12) to OX40R-IgG1 (A) sequence of peptide P5 (SEQ ID NO: 6), aligned with mouse OX40L-derived peptide P-OX-1 (SEQ ID NO: 14) (Stuber E and Strober W, 1996; indicates non conservative substitution and indicates conservative substitutions, as indicated in Table I) and with the sequence of the P5-derived peptides tested with the Alphascreen™-based competition assay. The peptide P5-1a is the boxed sequence in P5-1. (B) Inhibition of binding of OX40R-IgG1 to OX40L-CD8 by the peptide P5-1 in the Alphascreen™-based competition assay, compared with the effect provided by other fragments of peptide P5.

On the basis of the sequence of the P5 peptide, a second series of partially overlapping peptides were tested to further reduce this inhibiting molecule (FIG. 6A; Table III). The result of this sequential screening is that the region comprised between amino acids 94 and 124 of human OX40L (P5) is not a minimal region since a peptide corresponding to amino acids 107-116 (P5-1), is capable to inhibit the binding of OX40R to OX40L still in the micromolar range (Kd~10 and 62 microMolar respectively). The other tested peptides showed no or hardly measurable effect on OX40R-OX40L interaction (FIG. 6B).

Since the P4 peptide, which contains the C-terminal six amino acids of P5-1 peptide, proved to bind OX40R very poorly, it can be also inferred that the N-terminal amino acids of P5-1 peptide, for example the sequence GYFSQ (peptide P5-1a; amino acids 107-111 in human OX40L; SEQ ID NO: 13), may represent a minimal peptide sequence functionally active as OX40R binding agent. When compared to the mouse OX40L-derived peptide P-OX-1 (Stuber E and Strober W, 1996), this peptide contains two non-conservative substitutions (FIG. 6A).

The sequences of P5 and P5-1 peptides identified in this example by competition assays allowed to identify structures in the OX40L which play an essential role in the OX40L-OX40R interaction, demonstrating that OX40L can be effectively competed by specific peptide sequences. These findings were not predictable from the analysis of the state of the art on the structure-activity relationship of these proteins, neither of other TNF/TNFR-like proteins, being the regions of contact between proteins belonging to these families very diverse amongst the pairs of ligands and receptors (Bodmer J L et al., 2002).

The affinity of the peptides identified in Example 1 as inhibitor of OX40L-OX40R interaction was evaluated by fluorescence quenching spectroscopy, a technology allowing such measurements in solution, under native conditions and without beads or other supports. This method is based on monitoring the changes in the intrinsic fluorescence of a protein (OX40R-IgG1) upon its binding with another protein (P5 or P5-1). Incubation of OX40R-IgG1 with increasing concentrations of P5 or P5-1 peptides caused a change of its intrinsic fluorescence in the form of an hyperbolic curve, when the changes in OX40R-IgG1 fluorescence were plotted against peptide P5 and P5-1 concentration (FIGS. 7A and 7B). Non-linear regression analysis of the data revealed an apparent dissociation constant for OX40R of KD~7.9 nM, and KD~24.6 nM for peptides P5 and P5-1, respectively. These values demonstrate a high affinity interaction between the OX40R-IgG1 and the selected peptides, which can be therefore used as OX40L antagonists.

The findings presented in this Example indicate that OX40R-OX40L interaction can be effectively inhibited by using specific OX40L-derived peptides which bind efficiently OX40R, providing novel opportunity for the development of drugs targeting the OX40R pathway and inhibiting aberrant or undesirable physiological events under its control. These OX40R binding agents can be then further characterized as antagonist of OX40L in its interaction with OX40R using the animal and cell biology assay known in the art (WO 99/42585; Imura A et al., 1997; Nohara C et al., 2001; Pippig S D et al., 1999; Kotani A. et al., 2002), and further validated by testing other potential use-limiting side-effects in relevant models (Coleman R A et al., 2001).

TABLE I

| Amino Acid | Synonymous Group | More Preferred Synonymous Groups |
|---|---|---|
| Ala | Gly, Thr, Pro, Ala, Ser | Gly, Ala |
| Arg | Asn, Lys, Gln, Arg, His | Arg, Lys, His |
| Asn | Glu, Asn, Asp, Gln | Asn, Gln |
| Asp | Glu, Asn, Asp, Gln | Asp, Glu |
| Cys | Ser, Thr, Cys | Cys |
| Gln | Glu, Asn, Asp, Gln | Asn, Gln |
| Glu | Glu, Asn, Asp, Gln | Asp, Glu |
| Gly | Ala, Thr, Pro, Ser, Gly | Gly, Ala |
| His | Asn, Lys, Gln, Arg, His | Arg, Lys, His |
| Ile | Phe, Ile, Val, Leu, Met | Ile, Val, Leu, Met |
| Leu | Phe, Ile, Val, Leu, Met | Ile, Val, Leu, Met |
| Lys | Asn, Lys, Gln, Arg, His | Arg, Lys, His |
| Met | Phe, Ile, Val, Leu, Met | Ile, Val, Leu, Met |
| Phe | Trp, Phe, Tyr | Tyr, Phe |
| Pro | Gly, Ala, Ser, Thr, Pro | Pro |
| Ser | Gly, Ala, Ser, Thr, Pro | Thr, Ser |
| Thr | Gly, Ala, Ser, Thr, Pro | Thr, Ser |
| Trp | Trp, Phe, Tyr | Trp |
| Tyr | Trp, Phe, Tyr | Phe, Tyr |
| Val | Met, Phe, Ile, Leu, Val | Met, Ile, Val, Leu |

TABLE II

| Amino Acid | Synonymous Group |
|---|---|
| Ser | D-Ser, Thr, D-Thr, allo-Thr, Met, D-Met, Met(O), D-Met(O), L-Cys, D-Cys |
| Arg | D-Arg, Lys, D-Lys, homo-Arg, D-homo-Arg, Met, Ile, D-.Met, D-Ile, Orn, D-Orn |
| Leu | D-Leu, Val, D-Val, AdaA, AdaG, Leu, D-Leu, Met, D-Met |
| Pro | D-Pro, L-I-thioazolidine-4-carboxylic acid, D-or L-1-oxazolidine-4-carboxylic acid |
| Thr | D-Thr, Ser, D-Ser, allo-Thr, Met, D-Met, Met(O), D-Met(O), Val, D-Val |
| Ala | D-Ala, Gly, Aib, B-Ala, Acp, L-Cys, D-Cys |
| Val | D-Val, Leu, D-Leu, Ile, D-Ile, Met, D-Met, AdaA, AdaG |
| Gly | Ala, D-Ala, Pro, D-Pro, Aib, .beta.-Ala, Acp |
| Ile | D-Ile, Val, D-Val, AdaA, AdaG, Leu, D-Leu, Met, D-Met |
| Phe | D-Phe, Tyr, D-Thr, L-Dopa, His, D-His, Trp, D-Trp, Trans-3,4, or 5-phenylproline, AdaA, AdaG, cis-3,4, or 5-phenylproline, Bpa, D-Bpa |
| Tyr | D-Tyr, Phe, D-Phe, L-Dopa, His, D-His |
| Cys | D-Cys, S--Me--Cys, Met, D-Met, Thr, D-Thr |
| Gln | D-Gln, Asn, D-Asn, Glu, D-Glu, Asp, D-Asp |
| Asn | D-Asn, Asp, D-Asp, Glu, D-Glu, Gln, D-Gln |
| Lys | D-Lys, Arg, D-Arg, homo-Arg, D-homo-Arg, Met, D-Met, Ile, D-Ile, Orn, D-Orn |

TABLE II-continued

| Amino Acid | Synonymous Group |
|---|---|
| Asp | D-Asp, D-Asn, Asn, Glu, D-Glu, Gln, D-Gln |
| Glu | D-Glu, D-Asp, Asp, Asn, D-Asn, Gln, D-Gln |
| Met | D-Met, S--Me--Cys, Ile, D-Ile, Leu, D-Leu, Val, D-Val |

TABLE III

| Peptide name | Peptide sequence | Correspondance with human OX40L |
|---|---|---|
| P1 (SEQ ID NO: 2) | VASLTYKDKVYLNVTTDNTSLDDFHVNGGEL | 150-180 |
| P2 (SEQ ID NO: 3) | LDDFHVNGGELILIHQNPGEFCVL | 160-183 |
| P3 (SEQ ID NO: 4) | VSHRYPRIQSIKVQFTEYKKEKGFILTSQ | 52-80 |
| P4 (SEQ ID NO: 5) | EKGFILTSQKEDEIMKVQNNSVIINCDGFYL | 72-102 |
| P5 (SEQ ID NO: 6) | IINCDGFYLISLKGYFSQEVNISLHYQKDEE | 94-124 |
| P6 (SEQ ID NO: 7) | HYQKDEEPLFQLKKRSVNSLMVASLTYKDK | 118-148 |
| P5-1 (SEQ ID NO: 8) | GYFSQEVNIS | 107-116 |
| P5-2 (SEQ ID NO: 9) | ISLHYQKDEE | 107-124 |
| P5-3 (SEQ ID NO: 10) | GFYLISLKGY | 99-108 |
| P5-4 (SEQ ID NO: 11) | QEVNISLHYQ | 111-120 |
| P5-5 (SEQ ID NO: 12) | IFNCDGFYLI | 94-103 |

REFERENCES

Al Shamkhani A et al., J Biol Chem, 272: 5275-5282, 1997.
Alzani R et al., Biochemistry, 34: 6344-6350, 1995.
Bansal-Pakala P et al., Nat Med, 7: 907-912, 2001.
Bodmer J L et al., Trends Bioch Sci, 27: 19-26, 2002.
Chen A et al., Immunity, 11: 689-698, 1999.
Cheng Y C and Prusoff W H, Biochem Pharmacol, 22: 3099-3108, 1973.
Cleland J L et al., Curr Opin Biotechnol, 12: 212-219, 2001.
Cochran A et al., Curr Opin Chem Biol, 5: 654-659, 2001.

Coleman R A et al., Drug Disc Today, 6: 1116-1125, 2001.
Constans A, The Scientist, 16: 37, 2002.
Dougherty D A, Curr Opin Chem Biol, 4: 645-652, 2000.
Godfrey W R et al., J Exp Med, 180: 757-762, 1994.
Golabek A et al., Biophys J, 79: 1008-1015, 2000.
Golebiowski A et al., Curr Opin Drug Discov Devel, 4: 428-434, 2001.
Gravestein L and Borst J, Semin Immunol, 10: 423-434, 1998.
Gray P W et al., Proc Natl Acad Sci, 87: 7380-7384, 1990.
Higgins L M et al., J Immunol, 162: 486-493, 1999.
Hruby V J and Balse P M, Curr Med Chem, 7: 945-970, 2000.
Imura A et al., Blood, 89: 2951-2958, 1997.
Kim H O and Kahn M, Comb Chem High Throughput Screen, 3: 167-183, 2000.
Kopf M et al., Immunity, 11: 699-708, 1999.
Kotani A et al., Immunol Lett, 84: 1-7, 2002.
Kraemer-Pecore C M et al., Cur Opin Chem Biol, 5: 690-695, 2001.
Lowe C R et al., J Biochem Biophys Methods, 49: 561-574, 2001.
Luo B and Prestwich G D, Exp Opin Ther Patents, 11: 1395-1410, 2001.
Makrides S C, Protein Expr Purif, 17: 183-202, 1999.
Miura S et al., Mol Cell Biol, 11: 1313-1325, 1991.
Murata K et al., J Exp Med, 191: 365-374, 2000.
Murphy L R et al., Protein Eng, 13: 149-152, 2000.
Nohara C et al., J Immunol, 166: 2108-2115, 2001.
Pillai O and Panchagnula R, Cur Opin Chem Biol, 5: 447-451, 2001.
Pippig S D et al., J Immunol, 163: 6520-6529, 1999.
Ranney D F, Biochem Pharmacol, 59: 105-114, 2000.
Rogov S I and Nekrasov A N, Protein Eng, 14: 459-463, 2001.
Sawyer T K, in "Structure Based Drug Design", edited by Veerapandian P, Marcel Dekker Inc., pg. 557-663, 1997.
Stuber E and Strober W, J Exp Med, 183: 979-989, 1996.
Taylor L and Schwarz H, J Imm Methods, 255: 67-72, 2001.
Taylor L et al, J Leuk Biol, 72: 522-529, 2002.
Tsukada N et al., Blood, 95: 2434-2439, 2000.
Ullman E et al., Proc Natl Acad Sci, 91: 5426-5430, 1994.
Villain Metal., Chem Biol, 8: 673-9, 2001.
Weinberg A et al., Nat Med, 2:183-189, 1996.
Weinberg A et al., J Immunol, 162: 1818-1826, 1999.
Weinberg A, Trends Immunol, 23: 102-109, 2002.
Yoshioka Y et al., Eur J Immunol, 30: 2815-2823, 2000.

We claim:

1. An isolated nucleic acid encoding a polypeptide consisting of:

a) SEQ ID NO: 6;

b) SEQ ID NO: 6, wherein one or more amino acids have been deleted, said polypeptide contains SEQ ID NO: 13 and said polypeptide binds to the OX40 receptor (OX40R);

c) between 5 and 10 contiguous amino acids of SEQ ID NO: 1, wherein said polypeptide contains SEQ ID NO: 13 and binds to OX40R;

d) SEQ ID NO: 8 or SEQ ID NO: 13;

e) an active mutant of a), b), c) or d), wherein one or more of the amino acids has been conservatively substituted and said active mutant binds to OX40R; or f) a fusion polypeptide or peptide comprising a first amino acid sequence and a second amino acid sequence, wherein said first amino acid sequence is a protein sequence other than human OX40L fused to a second amino acid sequence selected from:

i) SEQ ID NO: 6;

ii) SEQ ID NO: 6, wherein one or more amino acids have been deleted, said second amino acid sequence contains SEQ ID NO: 13 and said fusion polypeptide binds to the OX40 receptor (OX40R);

iii) between 5 and 10 contiguous amino acids of SEQ ID NO: 1, wherein said contiguous amino acids of SEQ ID NO: 1 contain SEQ ID NO: 13 and said fusion polypeptide binds to OX40R; or iv) SEQ ID NO: 8 or SEQ ID NO: 13.

2. The isolated nucleic acid according to claim 1, wherein said nucleic acid encodes a fusion polypeptide or peptide that comprises an amino acid sequence selected from one or more of the following protein sequences: membrane-bound proteins, extracellular domains of membrane-bound protein, immunoglobulin constant region, multimerization domains, extracellular proteins, signal peptide-containing proteins or export signal-containing proteins.

3. The isolated nucleic acid according to claim 1, wherein said nucleic acid encodes a polypeptide consisting of SEQ ID NO: 6.

4. The isolated nucleic acid according to claim 1, wherein said nucleic acid encodes a polypeptide consisting of SEQ ID NO: 6, wherein one or more amino acids have been deleted, said polypeptide contains SEQ ID NO: 13 and said polypeptide binds to the OX40 receptor (OX40R).

5. The isolated nucleic acid according to claim 1, wherein said nucleic acid encodes a polypeptide consisting of between 5 and 10 contiguous amino acids of SEQ ID NO: 1, containing SEQ ID NO: 13 and binding to OX40R.

6. The isolated nucleic acid according to claim 1, wherein said nucleic acid encodes a polypeptide consisting of SEQ ID NO: 8.

7. The isolated nucleic acid according to claim 1, wherein said nucleic acid encodes a polypeptide consisting of SEQ ID NO: 13.

8. The isolated nucleic acid according to claim 1, wherein said nucleic acid encodes a polypeptide consisting of an active mutant of a), b), c) or d), wherein three or fewer amino acids are conservatively substituted and said active mutant binds to OX40R.

9. The isolated nucleic acid according to claim 1, wherein said nucleic acid encodes a fusion polypeptide or peptide and said second amino acid sequence is a peptide consisting of SEQ ID NO: 6.

10. The isolated nucleic acid according to claim 1, wherein said nucleic acid encodes a fusion polypeptide or peptide and said second amino acid sequence is SEQ ID NO: 6, wherein one or more amino acids have been deleted, said polypeptide contains SEQ ID NO: 13 and said fusion polypeptide or peptide binds to the OX40 receptor (OX40R).

11. The isolated nucleic acid according to claim 1, wherein said nucleic acid encodes a fusion polypeptide or peptide and said second amino acid sequence is a peptide consisting of between 5 and 10 contiguous amino acids of SEQ ID NO: 1 that contains SEQ ID NO: 13 and said fusion polypeptide or peptide binds to OX40R.

12. The isolated nucleic acid according to claim 1, wherein said nucleic acid encodes a fusion polypeptide or peptide and said second amino acid sequence is a peptide consisting of SEQ ID NO: 8 or SEQ ID NO: 13.

13. The isolated nucleic acid according to claim 1, wherein said nucleic acid encodes a polypeptide that antagonizes the activity of OX40R.

14. A vector comprising the nucleic acid according to claim 1.

15. A host cell comprising a nucleic acid according to claim 1.

16. A method of making a polypeptide comprising culturing the host cell according to claim 15 under conditions that allow for the production of a polypeptide consisting of:

a) SEQ ID NO: 6;

b) SEQ ID NO: 6, wherein one or more amino acids have been deleted, said polypeptide contains SEQ ID NO: 13 and said polypeptide binds to the OX40 receptor (OX40R);

c) between 5 and 10 contiguous amino acids of SEQ ID NO: 1, wherein said polypeptide contains SEQ ID NO: 13 and binds to OX40R;

d) SEQ ID NO: 8 or SEQ ID NO: 13;

e) an active mutant of a), b), c) or d), wherein one or more of the amino acids has been conservatively substituted and said active mutant binds to OX40R; or f) a fusion polypeptide or peptide comprising a first amino acid sequence and a second amino acid sequence, wherein said first amino acid sequence is a protein sequence other than human OX40L fused to a second amino acid sequence selected from:

i) SEQ ID NO: 6;

ii) SEQ ID NO: 6, wherein one or more amino acids have been deleted, said second amino acid sequence contains SEQ ID NO: 13 and said fusion polypeptide binds to the OX40 receptor (OX40R);

iii) between 5 and 10 contiguous amino acids of SEQ ID NO: 1, wherein said contiguous amino acids of SEQ ID NO: 1 contain SEQ ID NO: 13 and said fusion polypeptide binds to OX40R; or iv) SEQ ID NO: 8 or SEQ ID NO: 13.

* * * * *

UNITED STATES PATENT AND TRADEMARK OFFICE

CERTIFICATE OF CORRECTION

PATENT NO. : 7,858,765 B2
APPLICATION NO. : 12/624534
DATED : December 28, 2010
INVENTOR(S) : Claudio Soto-Jara and Claudia Pena-Rossi It is certified that error appears in the above-identified patent and that said Letters Patent is hereby corrected as shown below:

Column 3,
Line 60, "and indicates" should read --and . indicates--.

Column 4,
Lines 66-67,
"http://npsa-pb ibcp.fr/cgi-bin/npsa_automat.pl?page=/NPSA/npsa_server.html"
should read
--http://npsa-pbil.ibcp.fr/cgi-bin/npsa_automat.pl?page=/NPSA/npsa_server.html--.

Column 11,
Line 23, "CD4" T cells" should read --CD4$^+$ T cells--.
Line 25, "CD4' T cells" should read --CD4$^+$ T cells--.

Column 14,
Line 59, "at ± 80° C" should read --at 80° C--.

Column 17,
Lines 2-3, "(1 mM ± 1 nM)" should read --(1 mM – 1 nM)--.

Column 20,
Line 51, "IFNCDGFYLI" should read --IINCDGFYLI--.

Signed and Sealed this
Fifteenth Day of March, 2011

David J. Kappos
*Director of the United States Patent and Trademark Office*

UNITED STATES PATENT AND TRADEMARK OFFICE

CERTIFICATE OF CORRECTION

PATENT NO. : 7,858,765 B2
APPLICATION NO. : 12/624534
DATED : December 28, 2010
INVENTOR(S) : Claudio Soto-Jara and Claudia Pena-Rossi It is certified that error appears in the above-identified patent and that said Letters Patent is hereby corrected as shown below:

Column 3,
Line 60, "and indicates" should read --and . indicates--.

Column 4,
Lines 66-67,
"http://npsa-pb ibcp.fr/cgi-bin/npsa_automat.pl?page=/NPSA/npsa_server.html"
should read
--http://npsa-pbil.ibcp.fr/cgi-bin/npsa_automat.pl?page=/NPSA/npsa_server.html--.

Column 11,
Line 23, "CD4" T cells" should read --$CD4^+$ T cells--.
Line 25, "CD4' T cells" should read --$CD4^+$ T cells--.

Column 14,
Line 59, "at ± 80° C" should read --at -80° C--.

Column 17,
Lines 2-3, "(1 mM ± 1 nM)" should read --(1 mM –1 nM)--.

Column 20,
Line 51, "IFNCDGFYLI" should read --IINCDGFYLI--.

This certificate supersedes the Certificate of Correction issued March 15, 2011.

Signed and Sealed this
Twenty-sixth Day of April, 2011

David J. Kappos

David J. Kappos
*Director of the United States Patent and Trademark Office*

```
                    SEQUENCE LISTING

<160> NUMBER OF SEQ ID NOS: 15

<210> SEQ ID NO 1
<211> LENGTH: 183
<212> TYPE: PRT
<213> ORGANISM: Homo sapiens

<400> SEQUENCE: 1

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180
```

-continued

```
<210> SEQ ID NO 2
<211> LENGTH: 31
<212> TYPE: PRT
<213> ORGANISM: Artificial sequence
<220> FEATURE:
<223> OTHER INFORMATION: human OX40R binding peptides

<400> SEQUENCE: 2

Val Ala Ser Leu Thr Tyr Lys Asp Lys Val Tyr Leu Asn Val Thr Thr
1               5                   10                  15

Asp Asn Thr Ser Leu Asp Asp Phe His Val Asn Gly Gly Glu Leu
            20                  25                  30


<210> SEQ ID NO 3
<211> LENGTH: 24
<212> TYPE: PRT
<213> ORGANISM: Artificial sequence
<220> FEATURE:
<223> OTHER INFORMATION: human OX40R binding peptides

<400> SEQUENCE: 3

Leu Asp Asp Phe His Val Asn Gly Gly Glu Leu Ile Leu Ile His Gln
1               5                   10                  15

Asn Pro Gly Glu Phe Cys Val Leu
            20


<210> SEQ ID NO 4
<211> LENGTH: 29
<212> TYPE: PRT
<213> ORGANISM: Artificial sequence
<220> FEATURE:
<223> OTHER INFORMATION: human OX40R binding peptides

<400> SEQUENCE: 4

Val Ser His Arg Tyr Pro Arg Ile Gln Ser Ile Lys Val Gln Phe Thr
1               5                   10                  15

Glu Tyr Lys Lys Glu Lys Gly Phe Ile Leu Thr Ser Gln
            20                  25


<210> SEQ ID NO 5
<211> LENGTH: 31
<212> TYPE: PRT
<213> ORGANISM: Artificial sequence
<220> FEATURE:
<223> OTHER INFORMATION: human OX40R binding peptides

<400> SEQUENCE: 5

Glu Lys Gly Phe Ile Leu Thr Ser Gln Lys Glu Asp Glu Ile Met Lys
1               5                   10                  15

Val Gln Asn Asn Ser Val Ile Ile Asn Cys Asp Gly Phe Tyr Leu
            20                  25                  30


<210> SEQ ID NO 6
<211> LENGTH: 31
<212> TYPE: PRT
<213> ORGANISM: Artificial sequence
<220> FEATURE:
<223> OTHER INFORMATION: human OX40R binding peptides

<400> SEQUENCE: 6

Ile Ile Asn Cys Asp Gly Phe Tyr Leu Ile Ser Leu Lys Gly Tyr Phe
1               5                   10                  15

Ser Gln Glu Val Asn Ile Ser Leu His Tyr Gln Lys Asp Glu Glu
            20                  25                  30
```

-continued

<210> SEQ ID NO 7
<211> LENGTH: 30
<212> TYPE: PRT
<213> ORGANISM: Artificial sequence
<220> FEATURE:
<223> OTHER INFORMATION: human OX40R binding peptides

<400> SEQUENCE: 7

```
His Tyr Gln Lys Asp Glu Glu Pro Leu Phe Gln Leu Lys Lys Arg Ser
1               5                   10                  15

Val Asn Ser Leu Met Val Ala Ser Leu Thr Tyr Lys Asp Lys
            20                  25                  30
```

<210> SEQ ID NO 8
<211> LENGTH: 10
<212> TYPE: PRT
<213> ORGANISM: Artificial sequence
<220> FEATURE:
<223> OTHER INFORMATION: human OX40R binding peptides

<400> SEQUENCE: 8

```
Gly Tyr Phe Ser Gln Glu Val Asn Ile Ser
1               5                   10
```

<210> SEQ ID NO 9
<211> LENGTH: 10
<212> TYPE: PRT
<213> ORGANISM: Artificial sequence
<220> FEATURE:
<223> OTHER INFORMATION: human OX40R binding peptides

<400> SEQUENCE: 9

```
Ile Ser Leu His Tyr Gln Lys Asp Glu Glu
1               5                   10
```

<210> SEQ ID NO 10
<211> LENGTH: 10
<212> TYPE: PRT
<213> ORGANISM: Artificial sequence
<220> FEATURE:
<223> OTHER INFORMATION: human OX40R binding peptides

<400> SEQUENCE: 10

```
Gly Phe Tyr Leu Ile Ser Leu Lys Gly Tyr
1               5                   10
```

<210> SEQ ID NO 11
<211> LENGTH: 10
<212> TYPE: PRT
<213> ORGANISM: Artificial sequence
<220> FEATURE:
<223> OTHER INFORMATION: human OX40R binding peptides

<400> SEQUENCE: 11

```
Gln Glu Val Asn Ile Ser Leu His Tyr Gln
1               5                   10
```

<210> SEQ ID NO 12
<211> LENGTH: 10
<212> TYPE: PRT
<213> ORGANISM: Artificial sequence
<220> FEATURE:
<223> OTHER INFORMATION: human OX40R binding peptides

<400> SEQUENCE: 12

```
Ile Ile Asn Cys Asp Gly Phe Tyr Leu Ile
```

-continued

```
1               5                   10


<210> SEQ ID NO 13
<211> LENGTH: 5
<212> TYPE: PRT
<213> ORGANISM: Artificial sequence
<220> FEATURE:
<223> OTHER INFORMATION: human OX40R binding peptides

<400> SEQUENCE: 13

Gly Tyr Phe Ser Gln
1               5


<210> SEQ ID NO 14
<211> LENGTH: 18
<212> TYPE: PRT
<213> ORGANISM: Artificial sequence
<220> FEATURE:
<223> OTHER INFORMATION: P-OX-1 peptide

<400> SEQUENCE: 14

Leu Lys Gly Ser Phe Phe Gln Glu Val Lys Ile Asp Leu His Phe Arg
1               5                   10                  15

Glu Asp


<210> SEQ ID NO 15
<211> LENGTH: 18
<212> TYPE: PRT
<213> ORGANISM: Artificial sequence
<220> FEATURE:
<223> OTHER INFORMATION: P-OX-2 peptide

<400> SEQUENCE: 15

Ala Phe Lys Asp Lys Val Tyr Leu Thr Val Asn Ala Pro Asp Thr Leu
1               5                   10                  15

Cys Glu
```